(12) United States Patent
Kreutzmann et al.

(10) Patent No.: US 9,119,930 B2
(45) Date of Patent: Sep. 1, 2015

(54) INHALATION THERAPY DEVICE COMPRISING A VALVE

(75) Inventors: Vera Kreutzmann, Seefeld (DE); Sven Rosenbeiger, Starnberg (DE); Markus Mornhinweg, Diessen (DE); Frank Kummer, Munich (DE); Titus Selzer, Munich (DE)

(73) Assignee: PARI GmbH Spezialisten für effektive Inhalation, Starnberg (DE)

( * ) Notice: Subject to any disclaimer, the term of this patent is extended or adjusted under 35 U.S.C. 154(b) by 623 days.

(21) Appl. No.: 12/889,846

(22) Filed: Sep. 24, 2010

(65) Prior Publication Data

US 2011/0209700 A1    Sep. 1, 2011

Related U.S. Application Data

(63) Continuation of application No. 10/574,517, filed as application No. PCT/EP2004/010084 on Sep. 9, 2004, now abandoned.

(30) Foreign Application Priority Data

Oct. 2, 2003    (DE) .................................. 103 45 950

(51) Int. Cl.
*A61M 11/00* (2006.01)
*A61M 15/00* (2006.01)
*A61M 11/06* (2006.01)

(52) U.S. Cl.
CPC ........... *A61M 11/06* (2013.01); *A61M 15/0013* (2014.02); *A61M 15/0018* (2014.02)

(58) Field of Classification Search
CPC ..... F16K 15/144; F16K 15/14; F16K 15/141; B65D 77/225; B65D 47/2031; B65D 47/2037; B65D 47/265; E03F 7/04; A47G 19/24; B29L 2031/565

USPC ............ 128/200.14, 200.16, 200.18, 200.21, 128/203.12, 203.14, 203.19; 137/852, 855; 222/490–491, 494

See application file for complete search history.

(56) References Cited

U.S. PATENT DOCUMENTS

| 3,861,386 A | 1/1975 | Harris et al. |
| 4,333,450 A | 6/1982 | Lester |

(Continued)

FOREIGN PATENT DOCUMENTS

| CA | 2124519 A1 | 11/1994 |
| CA | 2389936 A1 | 5/2001 |

(Continued)

OTHER PUBLICATIONS

Search Report mailed Dec. 30, 2004 from corresponding International Application No. PCT/EP2004/010084.

(Continued)

*Primary Examiner* — Rachel Young
(74) *Attorney, Agent, or Firm* — Wolf, Greenfield & Sacks, P.C.

(57) ABSTRACT

The inhalation therapy device according to the invention comprises a nebulizer chamber which accommodates an aerosol generator that emits aerosol into the nebulizer chamber. A valve that has a valve seat, a resilient valve member and a valve member positioning means is arranged at an opening of the nebulizer chamber. The valve member positioning means can be moved out of a first position and into a second position so as to position the valve member on the valve seat in such a manner that in the first position, the valve member, in a flow-free state, is positioned on the valve seat in a pretensioned manner and in a second position, is spaced apart from the valve seat.

37 Claims, 12 Drawing Sheets

(56) References Cited

U.S. PATENT DOCUMENTS

| | | | |
|---|---|---|---|
| 4,429,835 A | | 2/1984 | Brugger et al. |
| 4,538,607 A | * | 9/1985 | Saul .................. 128/207.16 |
| 4,674,691 A | | 6/1987 | Didion |
| 4,825,863 A | | 5/1989 | Dittmar et al. |
| 4,834,083 A | | 5/1989 | Byram et al. |
| 4,877,989 A | | 10/1989 | Drews et al. |
| 5,209,225 A | | 5/1993 | Glenn |
| D355,029 S | | 1/1995 | Kinneir et al. |
| 5,501,348 A | | 3/1996 | Takeuchi |
| 5,549,102 A | | 8/1996 | Lint et al. |
| 5,584,285 A | * | 12/1996 | Salter et al. .............. 128/200.21 |
| 5,685,294 A | | 11/1997 | Gupte et al. |
| 5,738,086 A | | 4/1998 | McMahon et al. |
| 5,826,571 A | | 10/1998 | Casper et al. |
| 5,865,353 A | | 2/1999 | Baudin |
| 5,950,848 A | | 9/1999 | Baudin |
| 5,954,049 A | | 9/1999 | Foley et al. |
| 5,957,389 A | | 9/1999 | Wunderlich et al. |
| 6,039,042 A | | 3/2000 | Sladek |
| 6,085,741 A | | 7/2000 | Becker |
| 6,176,237 B1 | | 1/2001 | Wunderlich et al. |
| 6,257,431 B1 | | 7/2001 | Baudin |
| 6,293,279 B1 | | 9/2001 | Schmitd et al. |
| 6,357,442 B1 | | 3/2002 | Casper et al. |
| 6,409,034 B2 | | 6/2002 | Schorner |
| 6,513,519 B2 | | 2/2003 | Gallem |
| 6,604,906 B2 | | 8/2003 | Ozeki et al. |
| 6,634,060 B1 | | 10/2003 | Lagler et al. |
| 6,637,432 B2 | | 10/2003 | Wakefield et al. |
| 6,708,688 B1 | | 3/2004 | Rubin et al. |
| 6,752,145 B1 | | 6/2004 | Bonney et al. |
| 6,904,906 B2 | | 6/2005 | Salter et al. |
| 6,962,151 B1 | | 11/2005 | Knoch et al. |
| 6,983,747 B2 | | 1/2006 | Gallem et al. |
| 7,131,440 B2 | | 11/2006 | Sonntag |
| 7,163,014 B2 | | 1/2007 | Nichols et al. |
| 7,305,986 B1 | | 12/2007 | Steiner et al. |
| 7,559,322 B2 | | 7/2009 | Foley et al. |
| 7,562,656 B2 | | 7/2009 | Gallem et al. |
| 7,600,511 B2 | | 10/2009 | Power et al. |
| RE43,289 E | * | 4/2012 | Bowers ...................... 137/855 |
| 2001/0013343 A1 | | 8/2001 | Andersson |
| 2002/0195109 A1 | * | 12/2002 | Mittelstadt et al. ...... 128/206.15 |
| 2003/0037785 A1 | | 2/2003 | Sonntag |
| 2003/0136399 A1 | | 7/2003 | Foley et al. |
| 2003/0226562 A1 | * | 12/2003 | Schmidt et al. .......... 128/200.24 |
| 2004/0040557 A1 | * | 3/2004 | Salter et al. .............. 128/203.12 |
| 2004/0094150 A1 | | 5/2004 | Flynn |
| 2004/0182387 A1 | | 9/2004 | Steiner et al. |
| 2009/0272820 A1 | | 11/2009 | Foley et al. |

FOREIGN PATENT DOCUMENTS

| | | |
|---|---|---|
| CA | 2064860 C | 3/2002 |
| DE | 1198298 B | 8/1965 |
| DE | 2231660 A | 1/1974 |
| DE | 3238149 A1 | 4/1984 |
| DE | 3429411 A1 | 2/1986 |
| DE | 3429389 C1 | 3/1986 |
| DE | G8703534.0 U1 | 9/1987 |
| DE | 3927170 A1 | 2/1991 |
| DE | 19500764 A1 | 7/1996 |
| DE | 19517102 A1 | 11/1996 |
| DE | 19902847 C1 | 5/2000 |
| DE | 19953317 C1 | 2/2001 |
| DE | 20221749 U1 | 6/2007 |
| EP | 0281650 B1 | 9/1988 |
| EP | 0626180 A1 | 11/1994 |
| EP | 0629560 A2 | 12/1994 |
| EP | 0826606 A1 | 3/1998 |
| EP | 0975526 B1 | 3/1998 |
| EP | 0976663 B2 | 2/2000 |
| EP | 0839735 B1 | 4/2000 |
| EP | 1075432 B1 | 9/2002 |
| EP | 1754500 B1 | 11/2008 |
| GB | 2358356 A | 7/2001 |
| JP | 10234827 | 2/1997 |
| WO | WO 86/01731 A1 | 9/1984 |
| WO | WO 01/49349 A1 | 7/2001 |
| WO | WO 02/40365 A1 | 5/2002 |
| WO | WO 03/05350 A1 | 1/2003 |
| WO | WO 2004/041336 A1 | 5/2004 |

OTHER PUBLICATIONS

International Preliminary Report on Patentability issued by WIPO dated Dec. 30, 2004 from corresponding International Application No. PCT/EP2004/010084.

International Preliminary Report on Patentability issued by WIPO dated Dec. 29, 2005 from corresponding International Application No. PCT/EP2004/010084.

Cipolla et al. "Characterization of aerosols of human recombinant deoxribonuclease I (rhDNase) generated by jet nebulizers" *Pharmaceutical Resarch*, 11:4 (1994).

Coates et al; CHEST Online; "A Comparison of the availability of tobramycin for inhalation from vented vs. unvented nebulizers" 113:951-956 (1998).

Eisenberg et al. "Chest Online; A Comparison of Peak Sputum Tobramycin concentration in patients with cystic fibrosis using jet and ultrasonic nebulizer systems" 111: 955-962 (1997).

Eklund et al. "The salt output of a nebulizer—a comparison between two nebulizer types" Respiratory Medicine 94:139-144 (2000).

Fiel et al., Chest Online; "A comparison of three jet nebulizer aerosol delivery systems used to administer recombinant human DNase 1 to patients with cystic fibrosis" 108:153-156 (1995).

Hess et al., Chest Online; "Medication nebulizer performance: effects of diluent volume nebulizer flow, and nebulizer brand" 110:498-505 (1996).

Le Brun "A review of the technical aspects of drug nebulization" 22:3, 75-81 (2000).

Loffert et al., Chest Online; "Comparison of commercial jet nebulizers" 106:1788-1792 (1994).

Niven, et al. "Some factors associated with the ultrasonic nebulization of proteins" *Pharmaceutical Research* 12:1, 53-59 (1995).

O'Callaghan, et al. "The Science of Nebulised drug delivery" *Thoras* 52:S31-S44 (1997).

Smith, et al. "Comparison of twenty three nebulizer/compressor combinations for domiciliary use" *Eur Respir. J.* 8:1214-1221 (1995).

Weber, et al. "Effect of nebulizer type and antibiotic concentration on device performance" *Pediatric Pulmonary* 23:249-260(1997).

Martin Knoch, "Potentials to Improve Nebulizer Systems for Solutions and Suspensions", Power Point Presentation, ISAM Congress, Vienna, Jun. 1999, 12 pages.

PARI Instructions for Use for PARI LC® PLUS, PARI LC® STAR Reusable Nebulizer pp. 1 thru 16, Aug. 2010.

* cited by examiner

INHALATION THERAPY DEVICE COMPRISING A VALVE

This application is a continuation of pending application Ser. No. 10/574,517, filed Jun. 20, 2007, which is hereby incorporated by reference in its entirety.

The invention relates to an inhalation therapy device comprising a valve, in particular an inhalation therapy device that comprises a valve and is easy to clean and simple and reliable to handle.

Inhalation therapy devices are used to administer suitable medicaments in the form of an aerosol to patients suffering from disorders of the respiratory tract. By adjusting the droplet size owing to a corresponding design of a nebulizer, it is possible to control those sites (pharynx, bronchi, lungs) at which the medicament is supposed to be deposited. The patient inhales the nebulized medicament through his mouth via a mouthpiece in order to adapt the inhalation therapy device to the patient to an optimum extent. To save the patient the trouble of having to remove the mouthpiece of the inhalation therapy device from his mouth between inhalation and exhalation, it is intended that the patient not only inhales the nebulized medicament from the inhalation therapy device, but also exhales back into the inhalation therapy device. The inhalation flow and the exhalation flow are usually controlled by valves in order to guide the air flow within the inhalation therapy device. For this purpose, so as to achieve optimum administration of a medicament while the patient is breathing in and out, the inhalation air and the exhalation air are guided in different ways so that the medicament in the inhalation therapy device is not contaminated by exhalation condensate during exhalation or guided with the exhalation flow out of the inhalation therapy device. For this purpose, it is necessary to provide valves on the inhalation therapy device in order to accordingly control the air flow during inhalation and exhalation.

The valves of an inhalation therapy device are usually exposed to contamination caused by residual medicament, sputum (saliva) and exhalation condensate. To comply with hygiene requirements, especially if the inhalation therapy device is being used by different patients, the valves, too, must therefore be cleaned regularly so as to free them of residual medicament, exhalation condensate and sputum residue. For this purpose, the valves should be designed such that they can be cleaned thoroughly in a simple manner. The valve housings and mounts nevertheless often comprise areas that can only be cleaned with difficulty or which are completely inaccessible and therefore virtually impossible to clean. This is particularly the case with valves in which the valve member cannot be removed from the valve seat since, for example, it is accommodated within a complex assembly or is securely connected.

Nevertheless, the valves must be easily attachable in order to avoid cumbersome handling of the device on the part of the user, which is particularly necessary in the case of patients whose respiratory disease places physical constraints on them, especially if they are elderly.

Furthermore, valve parts, in particular the valve member, must be prevented at all costs from becoming detached from the valve and being swallowed by the patient during inhalation. Since the patient often breathes in deeply during inhalation therapy, swallowing or inhalation of a valve member would have potentially life-threatening consequences because this valve member could be sucked deep into the lungs with the inhalation flow.

Inhalation therapy devices that are equipped with a valve are known in the prior art. These valves are used to direct the air flow within an inhalation therapy device so that the air flows in accordance with the function of the inhalation therapy device. An aerosol generator emits an aerosol into a nebulizer chamber. This aerosol is entrained by the inhalation air flow and applied within the patient as a result of inhalation. An inhalation valve thereby prevents the aerosol from being released into the environment, for example owing to a lack of air flow, such as during pauses in breath or during exhalation processes with a reversed air flow, in that the valve only permits air to flow from the outside into the nebulizer chamber. Exhalation valves are also used, which serve to reduce overpressure whenever the patient exhales into the inhalation therapy device by releasing exhalation air into the environment, or which serve to prevent the exhalation air from flowing via the inhalation path. The valves (inhalation valve and exhalation valve) are, moreover, also intended to prevent exhalation air from being misdirected and the medicament from being entrained out of the inhalation therapy device into the environment.

Furthermore, a portable nebulizer chamber for an inhaler is known from U.S. Pat. No. 6,039,042, in which a mouthpiece can be removed from a nebulizer chamber, with the valve seat being located on the nebulizer chamber and the valve member being attached to the mouthpiece.

Moreover, an inhalation nebulizer is known from DE 199 53 317 C1, in which a valve member and a valve seat are attached to a lid that can be removed from an inhalation nebulizer, with both the valve member and the valve seat being located on the lid.

In addition, a nebulizer distributor is known from U.S. Pat. No. 4,333,450, in which a nebulizer comprising a nebulizer chamber is described, said nebulizer being provided with a lid to which a valve member is attached that, in a closed state, lies on a valve seat arranged on the nebulizer housing.

These valves of inhalation therapy devices according to the prior art are either easily detachable, in which case they do, however, contain parts that could be easily swallowed by the patient if they are not secured properly, or they can be taken apart and reassembled only with a great deal of time and effort, which makes handling far from simple and often results in the loss of the characteristic that the valve can be cleaned in a simple manner. As a rule, the critical areas of a valve in terms of contamination in the region of the seal seat or an attachment are not accessible for cleaning because the valves often have a compact structural design.

It is the object of the present invention to eliminate the disadvantages of the inhalation therapy devices according to the prior art and to provide an inhalation therapy device having a valve that is easy to clean owing to its construction and is reliable and simple to handle.

This object is solved by an inhalation therapy device having a nebulizer chamber, an aerosol generator arranged so as to emit a generated aerosol into the nebulizer chamber, at least one opening in a wall of the nebulizer chamber and at least one valve arranged on the at least one opening in the wall of the nebulizer chamber, with the valve comprising a valve seat, a resilient valve member and a valve member positioning means, whereby the valve member positioning means can be moved, relative to the valve seat and valve member, out of a first position and into a second position such that in the first position, the valve member, in a flow-free state, is positioned on the valve seat by the valve member positioning means and in the second position, the valve member is spaced apart from the valve seat.

The valve member positioning means according to the invention enables the valve member to be designed and arranged so as to be spaced apart from the opened nebulizer.

In this position, the nebulizer as well as the valve can be cleaned easily. In the closed state, the valve member positioning means has a positional effect on the valve member and moves it onto the valve seat, from which it is spaced apart in the opened state. The position at which the valve seat, valve member and valve member positioning means are attached to the nebulizer can be chosen more or less at will, provided that the inventive action of the valve member positioning means upon the valve member is realized when moving the valve member positioning means out of the second position and into the first position.

The aforementioned object is, moreover, solved by an inhalation therapy device that has a nebulizer chamber, an aerosol generator arranged so as to emit a generated aerosol into the nebulizer chamber, at least one opening in a wall of the nebulizer chamber and at least one valve arranged on the at least one opening in the wall of the nebulizer chamber, with the valve comprising a valve seat and a resilient valve member, whereby the valve seat can be moved, relative to the valve member, out of a first position and into a second position such that in the first position, the valve member, in a flow-free state, is positioned on the valve seat and in the second position, the valve member is spaced apart from the valve seat.

Even without a valve member positioning means, the alternative solution according to the invention enables the valve member to be designed and arranged so as to be spaced apart from the opened nebulizer. In this position, the nebulizer as well as the valve can be cleaned easily. In the closed state, the corresponding attachment of the valve member has a positional effect on the valve member even without a valve member positioning means and moves it onto the valve seat, from which it is spaced apart in the open state. The position at which the valve seat and valve member are attached to the nebulizer can be chosen more or less at will, provided that even without the valve member positioning means, the inventive action of the attachment of the valve member upon the valve member is realized when moving the valve seat, relative to the valve member, out of the second position and into the first position.

Further advantageous embodiments can be seen in the sub-claims.

For example, the spacing apart of the valve member can be achieved by means of a correspondingly designed fixing of the valve member. This approach makes use of the resilience of the valve member, which moves into the spaced-apart position of its own accord whenever the valve member positioning means is not acting upon the valve member.

The resilience of the valve member can, however, also be utilized when there is no valve member positioning means, thereby causing the valve member to move into the spaced-apart position of its own accord. The resilient forces inherent in the valve member can, for instance, cause the valve member to be oriented in a straight line, in which case the valve member assumes the spaced-apart position according to the invention.

The pre-tension is advantageously produced by bending the valve member, for which purpose the valve seat may have a curved, rounded or sloping design in order to bend the valve member that is positioned on the valve seat so as to produce the pre-tension.

The valve according to the invention can be located anywhere on the inhalation device. That portion of the wall in which the opening and hence the valve are located can advantageously move relative to the nebulizer chamber. This wall portion is preferably a lid that closes the nebulizer chamber. The lid can be attached to a stationary part of the nebulizer chamber in a fold-down manner, said attachment being effected by means of a film hinge that can also be designed as a bi-stable film hinge.

Particularly advantageous is an embodiment of the inhalation therapy device according to the invention in which the valve seat and the valve member positioning means, on the one hand, and the valve member, on the other hand, are injection-moulded as a single part from different materials. Generally, the valve member is made of a softer material, such as silicone rubber or a thermoplastic elastomer, than the valve seat and/or the valve member positioning means.

In a further advantageous embodiment of the inhalation therapy device according to the invention, the valve seat and valve member are injection-moulded as a single part from different materials. In this case, the valve member is usually made of a softer material, for example silicone rubber or a thermoplastic elastomer, than the valve seat.

To assist the sealing function of the valve member, a circumferential sealing lip can be provided on the valve seat.

It must be noted that the valve according to the invention can be used as an inhalation valve or as an exhalation valve.

The invention will be described in more detail below on the basis of embodiments and with reference to the drawings. In the drawings, FIG. 1 shows an inhalation therapy device having an integrated valve in accordance with a first embodiment of the present invention;

FIG. 2*a* shows a valve in accordance with the first embodiment of the present invention in a closed, flow-free state;

FIG. 2*b* shows a valve in accordance with the first embodiment of the present invention in an opened state;

FIG. 2*c* shows a valve in accordance with the first embodiment of the present invention in a state of downwards flow;

FIG. 3*a* shows a valve in accordance with a second embodiment of the present invention in a closed state;

FIG. 3*b* shows a valve in accordance with the second embodiment of the present invention in an opened state;

FIG. 4*a* shows a valve in accordance with a third embodiment of the present invention in a closed state;

FIG. 4*b* shows a valve in accordance with the third embodiment of the present invention in an opened state;

FIG. 5*a* shows a valve in accordance with a fourth embodiment of the present invention in a closed state;

FIG. 5*b* shows a valve in accordance with the fourth embodiment of the present invention in an opened state;

FIG. 6*a* shows a valve in accordance with a fifth embodiment of the present invention in a closed state;

FIG. 6*b* shows a valve in accordance with the fifth embodiment of the present invention in an opened state;

FIG. 7*a* shows a valve in accordance with a sixth embodiment of the present invention in a closed state;

FIG. 7*b* shows a valve in accordance with the sixth embodiment of the present invention in an opened state;

FIG. 8*a* shows a valve in accordance with a further embodiment of the present invention having a bi-stable film hinge in a closed state;

FIG. 8*b* shows a valve in accordance with the further embodiment of the present invention having a bi-stable film hinge in an opened state;

FIG. 9*a* shows a valve in accordance with a further embodiment of the present invention in which the valve member abuts, without pre-tension, the valve seat, without an air flow;

FIG. 9*b* shows a valve in accordance with the further embodiment of the present invention in which the valve member abuts, without pre-tension, the valve seat, with air flowing into the inhalation therapy device;

Figure 1:
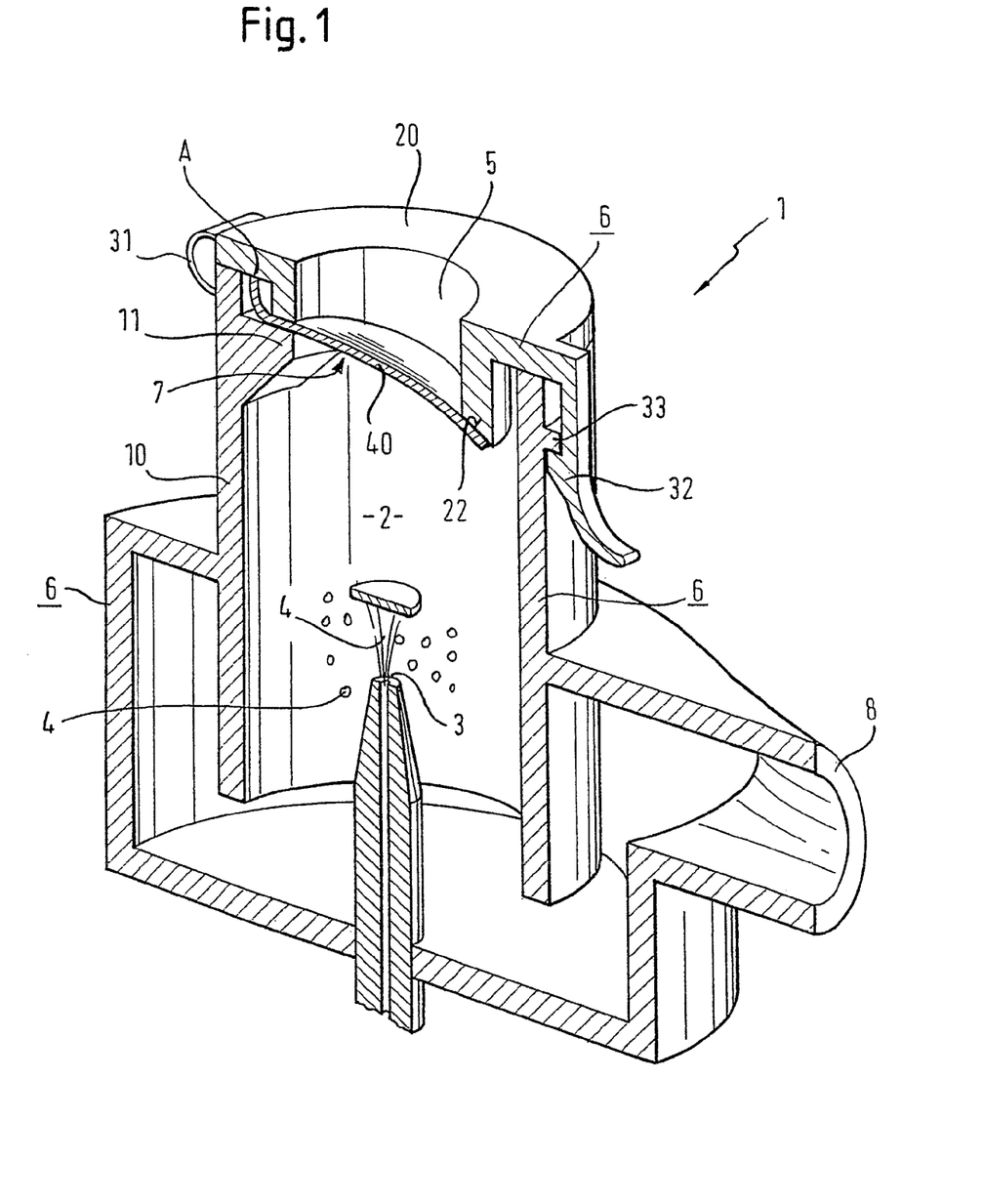

FIG. 1 shows an inhalation therapy device 1 in accordance with an embodiment of the present invention. The inhalation therapy device 1 has a nebulizer chamber 2 into which an aerosol generator 3 generates an aerosol 4. This aerosol 4 is stored in the nebulizer chamber 2. A first portion 10 of the wall 6 of the inhalation therapy device 1 is stationary; a second portion 20 of the wall 6 of the inhalation therapy device 1 can move relative to the first portion 10. The movable portion 20 of the wall 6 is designed as a lid in this embodiment. An opening 5, in which a valve 7 is disposed, is provided in the movable wall portion 20. The valve comprises a valve seat 22, a valve member 40 and a valve member positioning means 11. In the closed state as shown in FIG. 1, the valve member positioning means 11 positions the valve member 40 on the valve seat 22 in such a way that the valve member 40 abuts the valve seat 22 with a slight pre-tension.

Pre-tension is applied to the valve member 40, for example, as a result of the fact that it is positioned along a curved valve seat 22 that rises on one side. As envisaged in the embodiment shown in FIG. 1, the valve member 40 can be securely connected to the lid 20 at a fixing point A in order to prevent the valve member from detaching and being lost. In terms of production, the so-called two-component injection moulding method, for example, is available for this purpose, with which it is possible for two or more suitable, albeit different materials, from which parts of an assembly are made, to be produced as a single part in an assembly. The parts of the assembly are then securely connected together and cannot become inadvertently detached from one another. In the present case, this ensures that parts cannot be lost and hence also ensures protection against unintentional inhalation. If the structure is designed suitably, the stationary part 10 of the inhalation therapy device 1, together with the movable part 20, can also be produced in this manner.

The valve member 40 is preferably made from a resilient material so that the deformability of the valve member 40 then ensures sealing on the valve seat 22. The resilient material may be a silicone rubber or a thermoplastic elastomer (TPE). The latter can be readily processed with less resilient materials, such as polyethylene (PE) or polypropylene (PP), in the two-component injection moulding method, such that the TPE parts and PE or PP parts are fixedly connected together.

If the patient inhales, for example, via a mouthpiece 8 when the lid 20 is closed, the breath produces a flow of respiratory air. The vacuum in the nebulizer chamber 2 causes the valve member 40 to be deflected and enables air from the area surrounding the inhalation therapy device 1 to flow into the nebulizer chamber 2. The flow of respiratory air through the opening 5, past the deflected valve member 40 and the aerosol generator 3, entrains the generated aerosol 4 and passes through the mouthpiece 8 to the patient.

Figure 2A:
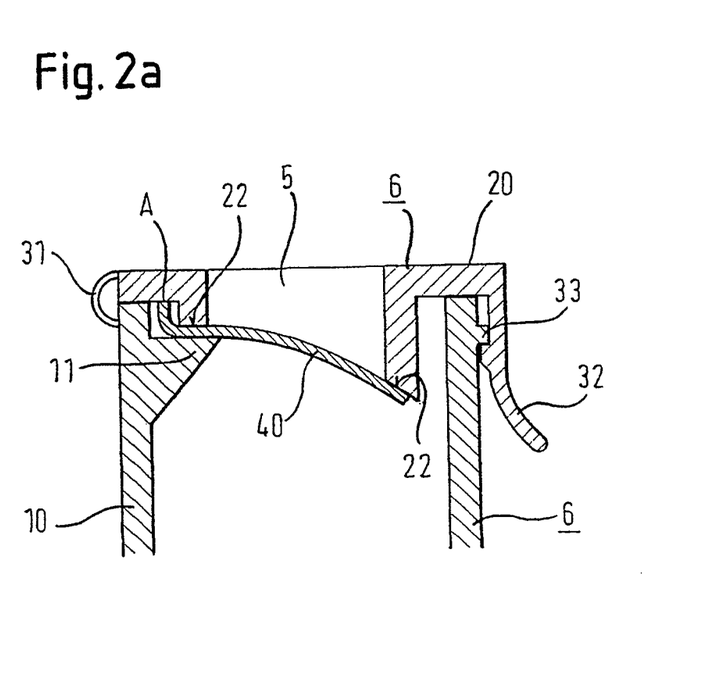

FIG. 2a, like FIG. 1, shows the valve in accordance with the present invention in a flow-free state. The wall 10 of the nebulizer chamber 2 of the inhalation therapy device 1 is closed by the movable lid 20, with the opening 5 being provided in said lid. The lid opening 5 is surrounded by the valve seat 22 on which the valve member 40 rests in the closed state. For this purpose, the valve member positioning means 11 holds the valve member 40 in such a position that the valve member 40 rests on the valve seat 22 in a slightly pre-tensioned manner in the flow-free state and essentially closes the opening 5. Herein, the lid is attached to the nebulizer chamber wall 10 of the inhalation therapy device 1 by means of a film hinge 31, and can be locked in the closed state by means of a snap lock 32, 33. The lid can be opened if the catch 32 of the snap lock is released from the notch 33. The valve member 40 is fixedly connected to the lid 20 at the fixing point A such that it cannot be released unintentionally. The valve seat 22 is designed in a sloped manner such that the valve member 40 abuts the valve seat 22 in a pre-tensioned manner in the flow-free state.

Figure 2B:
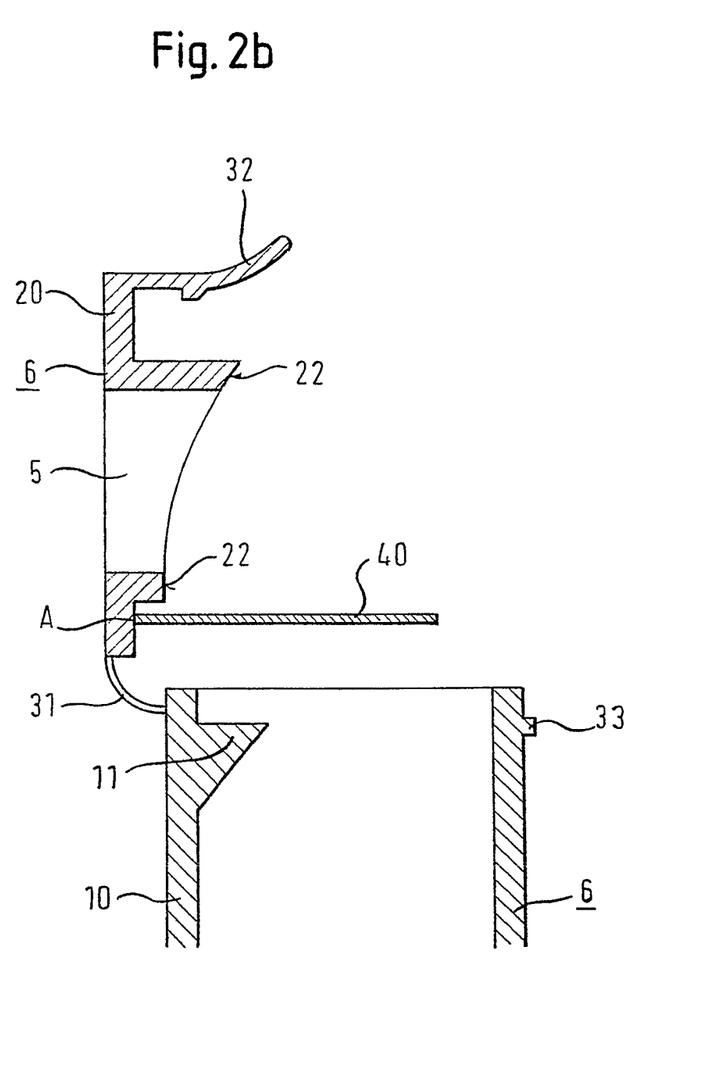

FIG. 2a shows the valve according to the invention in a closed state which is ready for use, whereas FIG. 2b shows the valve in an opened state for cleaning purposes. Since the resilient valve member 40, which is attached perpendicular to the lid 20 in this embodiment, is preferably moulded on, the valve member moves out of the position abutting the valve seat 22 since when the lid 20 is open, the valve member positioning means 11 no longer holds the valve member 40 in the sealing position on the valve seat 22 in a pre-tensioned manner. When the lid 20 is open, the valve member 40, in accordance with the invention, is spaced apart from the valve seat 22 such that both the valve seat 22 as well as the valve member 40 and valve member positioning means 11 are accessible and can be easily cleaned without there being any edges or concealed areas which make cleaning accordingly difficult or impossible.

Figure 2C:
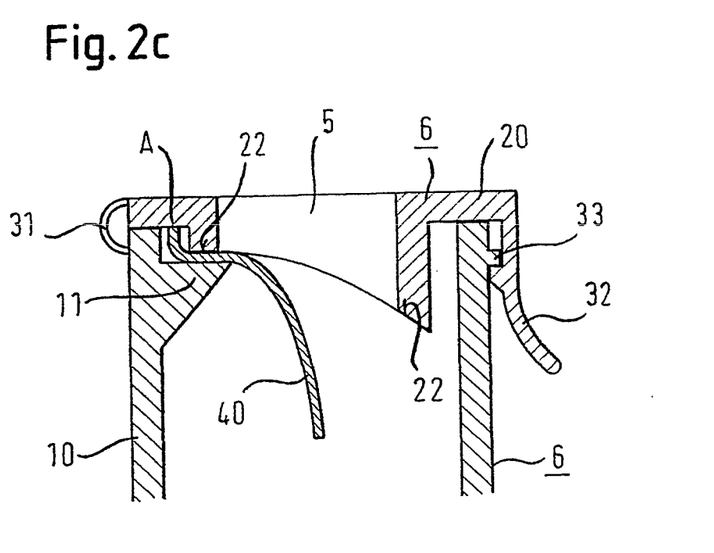

FIG. 2c shows the valve of FIG. 2a in a state in which air flows through the opening 5 and hence through the opened valve. The air flow deflects the valve member 40 such that it is deflected out of a state that closes the nebulizer chamber 2 and into a state that does not close the nebulizer chamber 2. If the flow of respiratory air is interrupted, the pre-tension causes the valve member 40 to return back to the starting position according to FIG. 2a and causes it to tightly abut the valve seat 22.

Figure 3A:
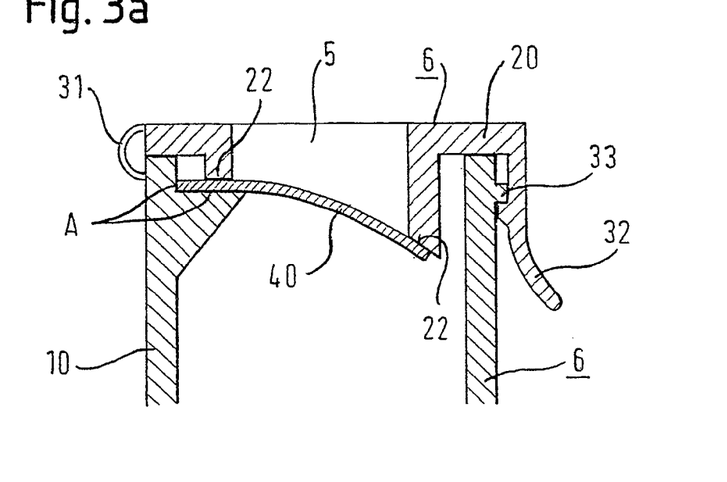
Figure 3B:
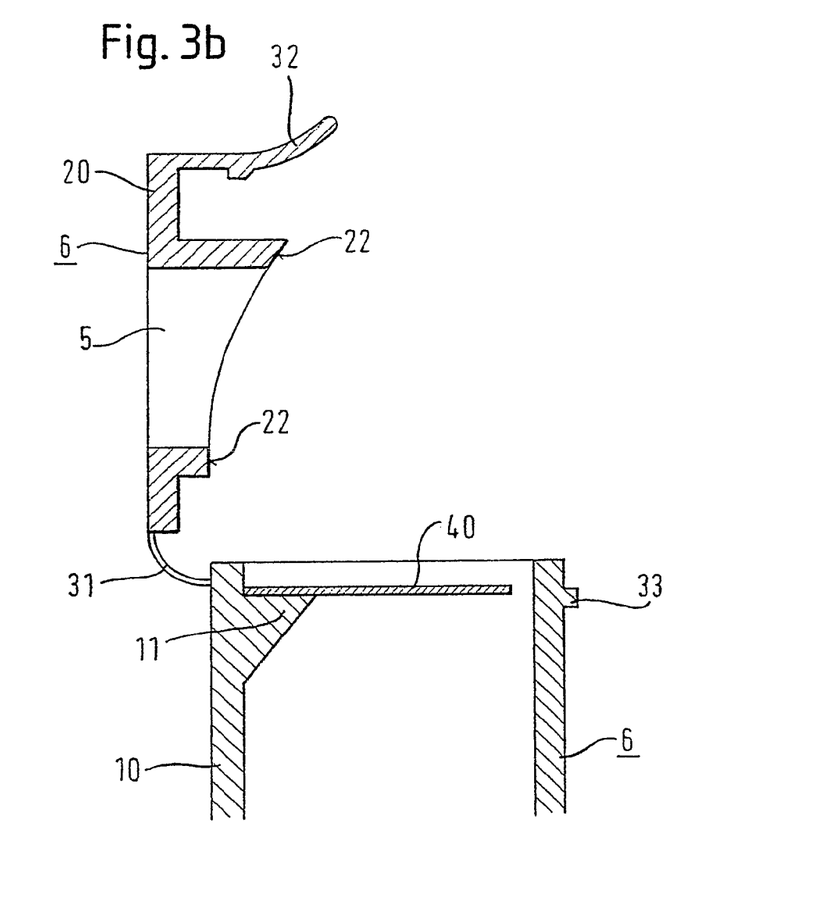

If the valve according to the invention is designed as an inhalation valve, the valve member 40 does not necessarily have to be attached to the lid 20. The valve member 40 can rather also be attached to the stationary part 10 of the inhalation therapy device 1 or to the valve member positioning means 11, as can be seen in FIG. 3a. In this case, the fixing point A can be provided on the wall of the nebulizer chamber 10 and/or on the valve member positioning means 11. The embodiment depicted in FIG. 3a is shown in FIG. 3b in an opened state. The valve member 40 is preferably secured to the stationary part 10 of the inhalation therapy device 1 close to the valve member positioning means 11 in such a way that no areas critical for cleaning arise. In this embodiment the valve seat 22 is, moreover, located on the movable part, i.e. on the lid 20, that is secured by means of a film hinge 31 to the stationary part, i.e. the wall 10 of the nebulizer chamber 2 of the inhalation therapy device.

The valve member 40 can be attached to the valve member positioning means 11 in a variety of ways, including in a detachable manner. However, a connection is preferably effected by means of a two-component production method (see above), which thus results in a particularly advantageous embodiment with regard to cleanliness. This is because at the joining point A between the valve member 40 and valve member positioning means 11, a connection is thus obtained over the entire surface area without any clearances or the formation of gaps.

Figure 4A:
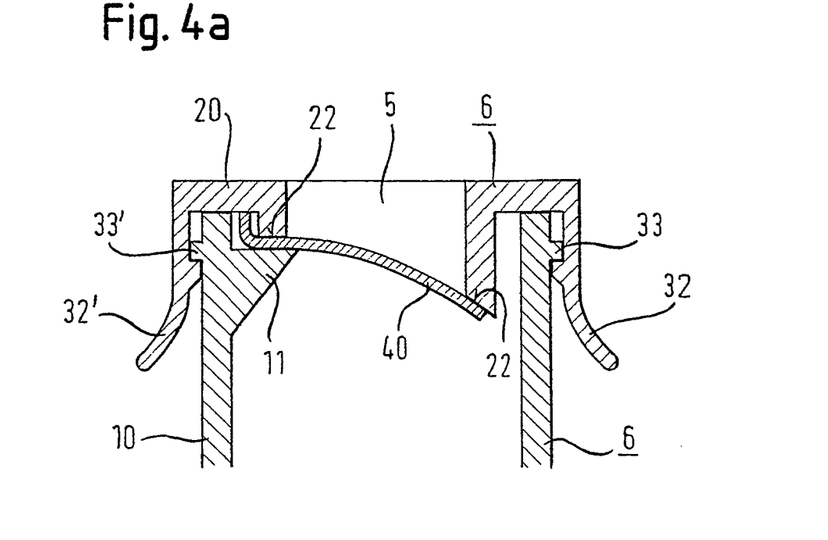
Figure 4B:
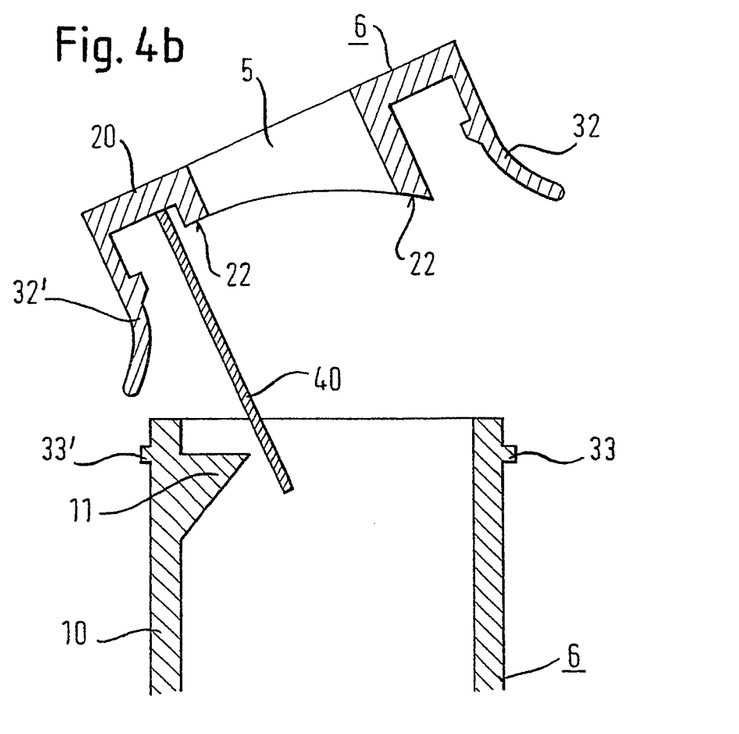
Figure 5A:
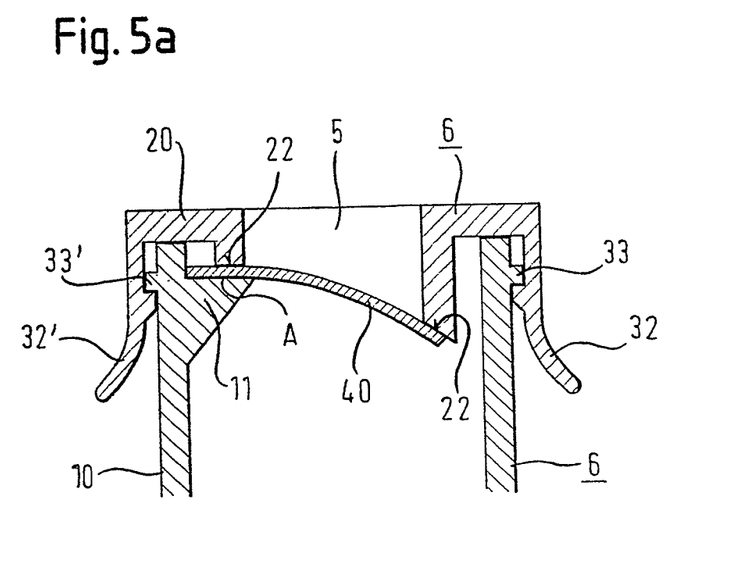
Figure 5B:
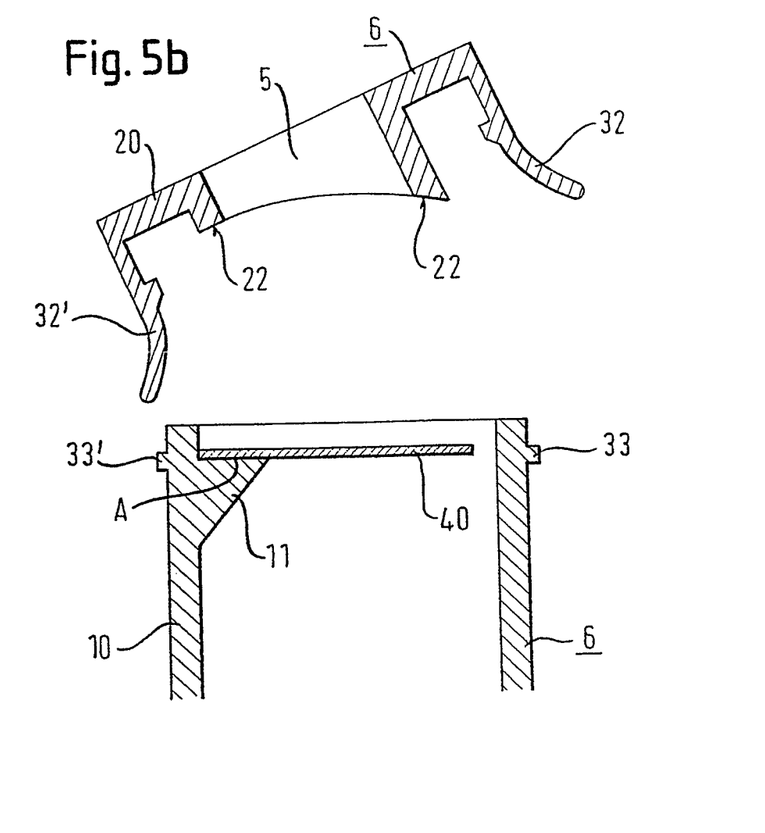

FIGS. 4a and 4b show an embodiment in which the lid 20 is not secured to the nebulizer chamber wall 10 of the inhalation therapy device 1 by means of a film hinge, but is rather mounted on the stationary part 10 of the inhalation therapy device 1 in the closed state by means of a second or plurality of further snap locks 32', 33' such that in accordance with the invention, the valve member 40 is positioned on the valve seat 22 by the valve member positioning means 11. Dispensing with a film hinge and instead using further snap connections or locks 32', 33' makes it possible to completely remove the lid 20 from the inhalation therapy device in order to be able to replace the lid, if need be, in the event of wear or contaminations that cannot be removed. Furthermore, in this embodiment, it is not absolutely necessary for the valve member 40 to be secured to the lid 20 close to the valve seat 22. The valve member 40, as already explained above, can also be mounted on the stationary part 10 of the inhalation therapy device or close to or on the valve member positioning means 11 in such a manner that it is not released unintentionally and so as not to produce any areas critical to cleaning, as shown in FIG. 5a in the closed state and in FIG. 5b in the opened state. This embodiment is advantageous if the valve member 40 does not have to be replaced and if other lids, for example lids provided with filters or respiratory flow restrictors, are to be attached to the upper section of the stationary part 10 of the inhalation therapy device.

Figure 6A:
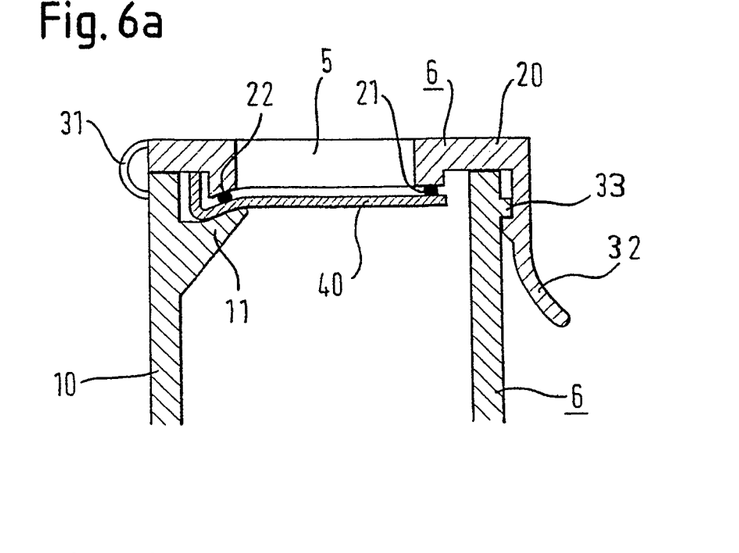
Figure 6B:
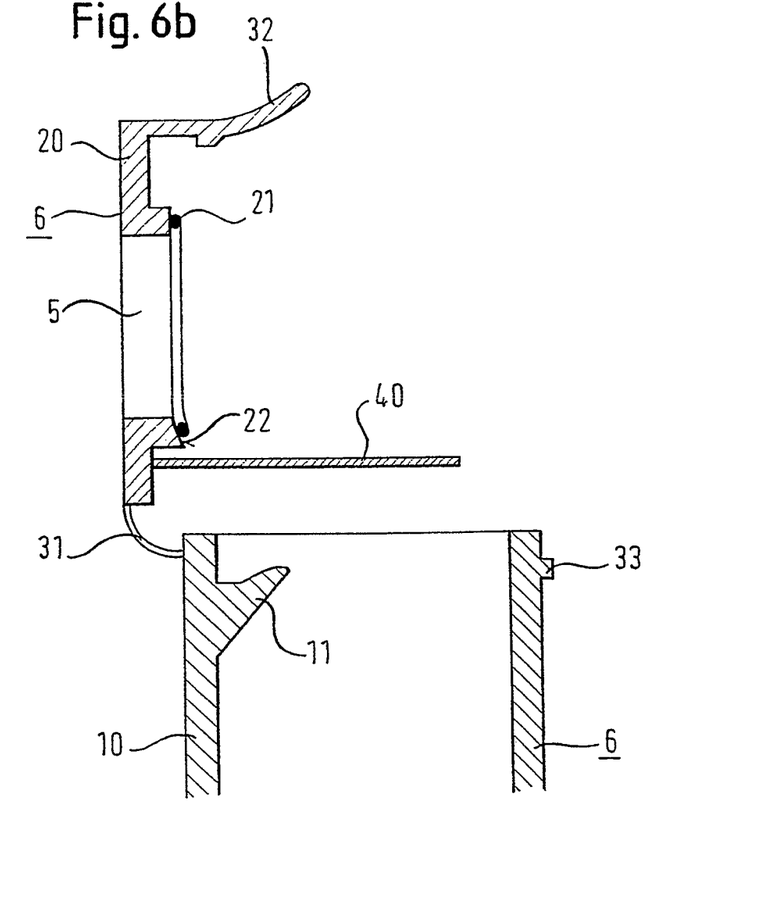

In a further advantageous embodiment, the valve seat 22 is not designed in a sloped manner, but is rather designed so as to be essentially linear, as shown by FIGS. 6a and 6b. In this case, to ensure that the valve member 40 is positioned in a sealing manner on the valve seat 22 with pre-tension, it is necessary to design the valve member positioning means 11 in such a way that pre-tension is achieved by suitable deformation of the resilient valve member 40 as a result of utilizing the resilience of the valve member. Of course, the valve member 40 can, in this embodiment, also be mounted on the stationary part 10 of the inhalation therapy device 1 or close to or on the valve member positioning means 11. FIGS. 6a and 6b also show a circumferential sealing lip 21 on the valve seat 22, which assists the sealing action of the valve member 40 on the valve seat 22. The sealing lip 21 is not restricted to use in a linear valve seat, but can also be provided when the valve seat is sloped or rounded, as described above.

Figure 7A:
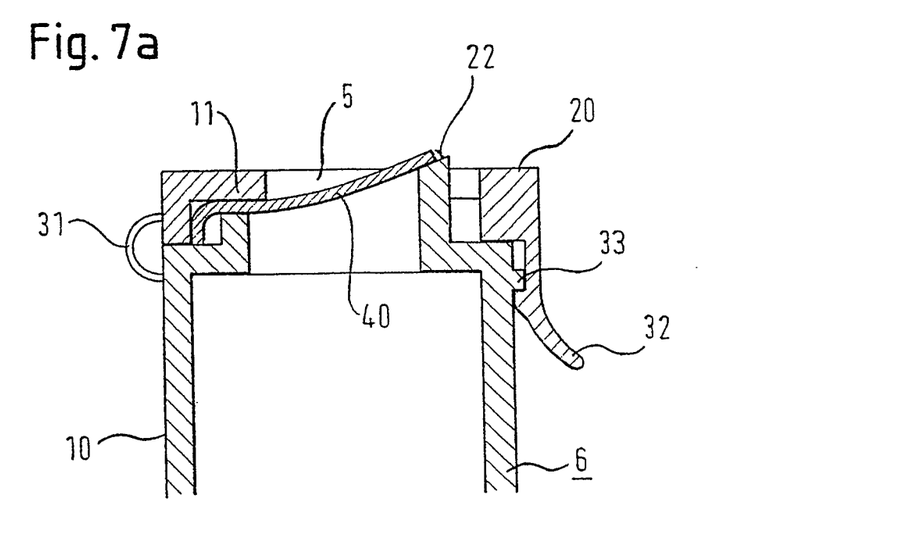
Figure 7B:
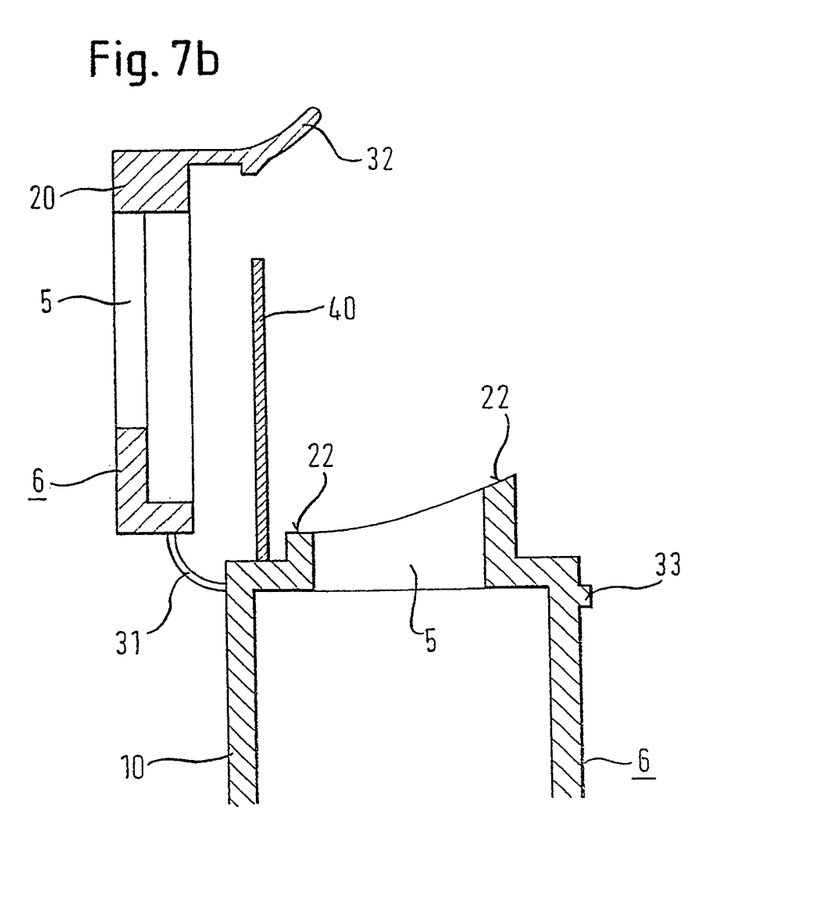

Whereas the embodiments described above relate to an inhalation valve, a valve according to the present invention will be described below as an exhalation valve. FIGS. 7a and 7b show such an exhalation valve in a closed and flow-free state and in an opened state for cleaning purposes, respectively. In this embodiment, the valve seat 22 is located on the stationary part 10 of the inhalation therapy device. The lid 20 is provided with the valve member positioning means 11 such that the valve member 40 is positioned on the valve seat 22 in a pre-tensioned manner in the closed state. In the opened state, the valve member 40 is spaced apart from the valve seat 22 owing to its attachment to the stationary part 10 of the inhalation therapy device and to its resilient material, such that it is possible to clean both the valve member 40 and the valve seat 22 easily, without producing any areas critical to cleaning.

As was the case with the embodiments described above, the valve member 40 can also be attached to or in the vicinity of the valve member positioning means 11.

The lid 20 can likewise be attached using further snap connections or locks 32, 33 so as to ensure the continued functioning of the valve member positioning means 11. In this case, however, the lid 20 can be removed completely from the stationary part 10 of the inhalation therapy device 1 so that this lid can be replaced if need be.

Figure 8A:
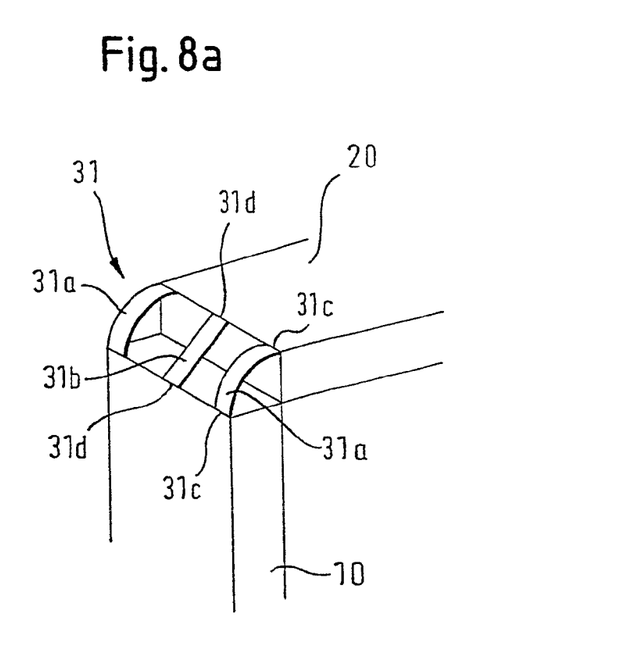
Figure 8B:
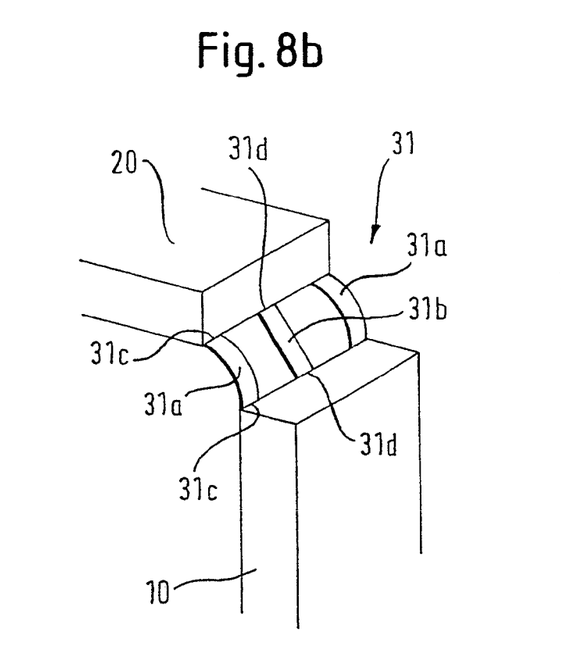

As shown in FIGS. 8a and 8b, the simple film hinge 31, which connects the lid 20 to the stationary part 10 of the inhalation therapy device, can be replaced by a bi-stable film hinge. This bi-stable film hinge has essentially two stable positions: one position in the closed state, whereby the lid 20 can then be locked by means of a snap connection 32, 33 in addition to the closing action of the film hinge, and one position in the opened state. The stabilized opened state ensures that the lid 20 does not unintentionally shut, for example during cleaning, and consequently hamper cleaning.

FIG. 8a schematically shows such a film hinge in a stable closed state and FIG. 8b schematically shows such a film hinge in a stable opened state. In one embodiment, the members 31a are curved and resilient, and the members 31b are straight and less resilient. At the points 31d, the member 31b is hingedly connected to the parts 10 and 20, whereas at the points 31c, the member 31a is rigidly connected to the parts 10 and 20, i.e. the attack angle between the surfaces of the parts 10 and 20 and the surfaces of the members 31a is not variable. The restoring force of the members 31a must be overcome by the movement from an opened position into a closed position so as to reach the stable closed position.

Figure 9A:
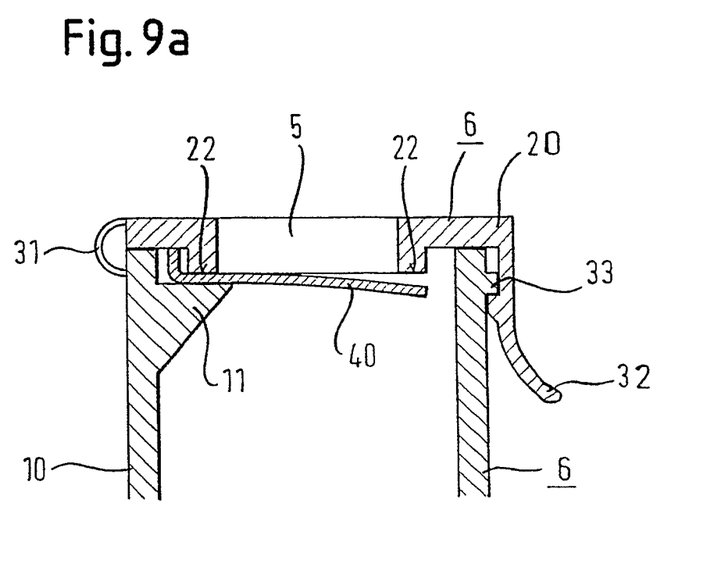
Figure 9B:
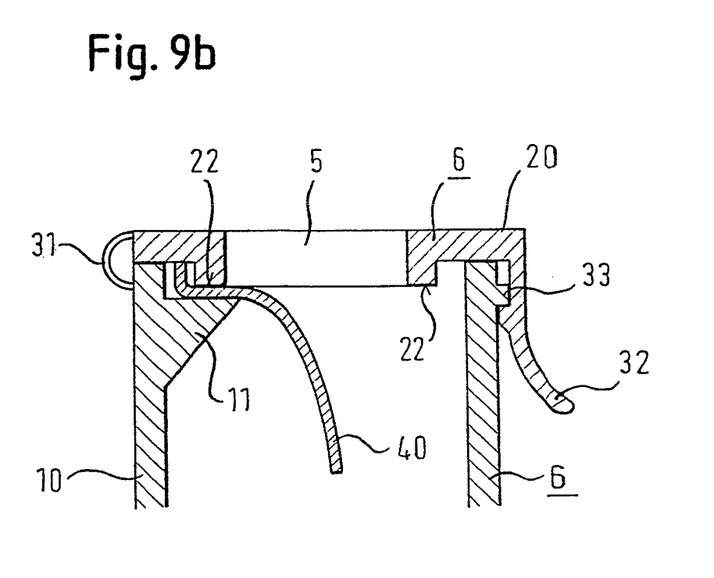

In a further preferred embodiment, the valve member 40 may abut the valve seat 22 even without pre-tension. In a flow-free state, as shown in FIG. 9a, it may happen that the valve member 40 is spaced apart from the valve seat 22 to a slight extent owing to gravity, however this does not impair the operability of the valve member and valve seat, since if there is a corresponding flow, the valve member, due to its low weight, is immediately deflected and then tightly abuts the valve seat 22. If there is a corresponding flow into the inhalation therapy device, the valve member 40, as already described above, is deflected so as to open the valve (FIG. 9b). In this case, the valve member positioning means 11 serves to move the valve member 40 into a corresponding position in which the valve member 40 is arranged at least close to the valve seat 22 in a closed state of the inhalation therapy device. Such an embodiment, in which the valve member 40 abuts the valve seat 22 without pre-tension, is particularly advantageous if the inhalation resistance is to be reduced, since the patient then does not have to breathe in through the valve against the pre-tension of the valve member.

Figure 10A:
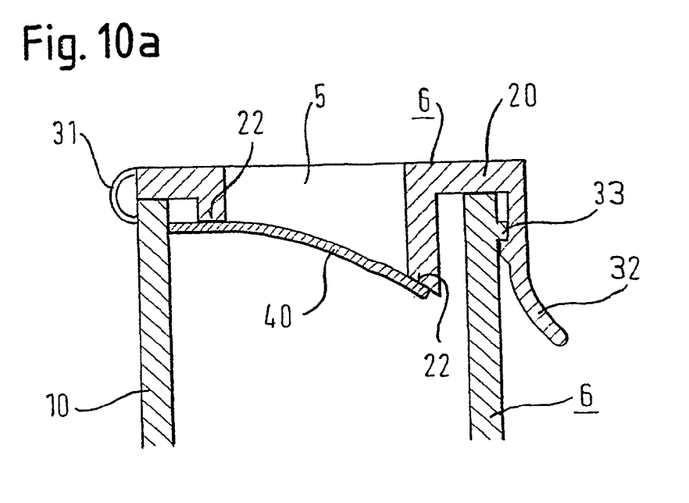
FIG. 10a shows a valve in accordance with a further embodiment of the present invention without a valve member positioning means, in which the valve member is secured to the stationary part of the inhalation therapy device in a closed state.
Figure 10B:
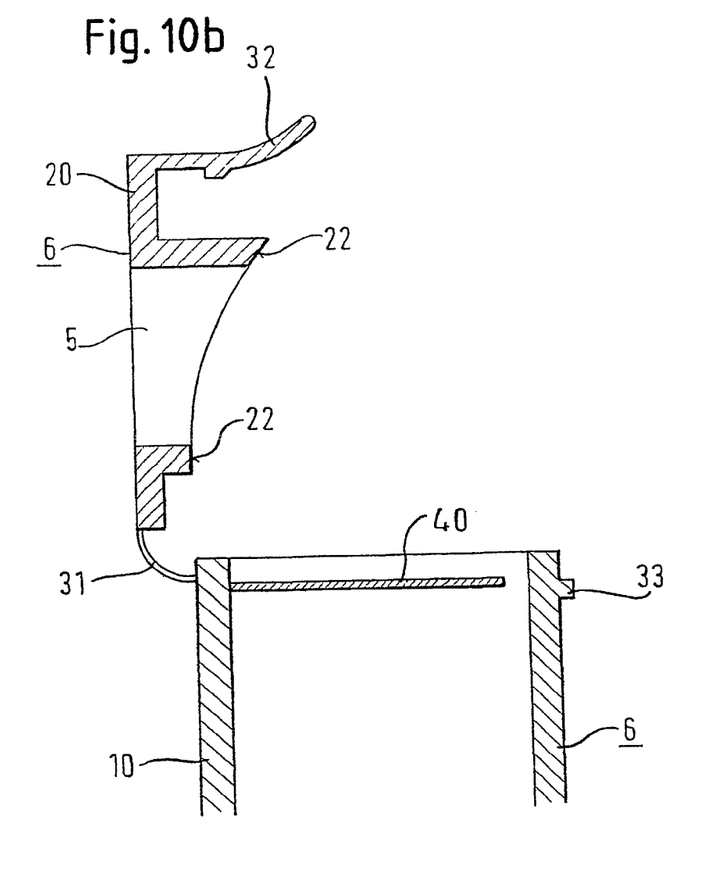
FIG. 10b shows a valve in accordance with the further embodiment of the present invention without a valve member positioning means, in which the valve member is secured to the stationary part of the inhalation therapy device in an opened state.

FIGS. 10a and 10b show a preferred embodiment in which the valve member 40 is moulded directly onto the stationary part 10 of the inhalation therapy device, such that it abuts the valve seat 22 without a valve member positioning means. In the embodiment shown here in FIG. 10a, the valve member 40 abuts the valve seat 22 in a pre-tensioned manner, but it should be emphasized that in this embodiment without valve member positioning means, the valve member 40 can abut the valve seat even without pre-tension if the valve seat is designed appropriately. FIG. 10b shows the preferred embodiment in an opened state in which the valve member 40 without a valve member positioning means is attached directly to the stationary part 10 of the inhalation therapy device so that, in the opened state, the inhalation therapy device does not have any sites on the valve seat 22 and valve member 40 that might be critical to cleaning. This embodiment can also be modified such that the movable part 20 of the inhalation therapy device can be secured to the stationary part 10 of the inhalation therapy device by means of two or more snap connections, as already described in a preceding embodiment. This makes it possible to replace the lid, for example with a linear valve seat in order to reduce the pre-tension of the valve member 40 on the valve seat 22, for instance to decrease the inhalation resistance.

Figure 11A:
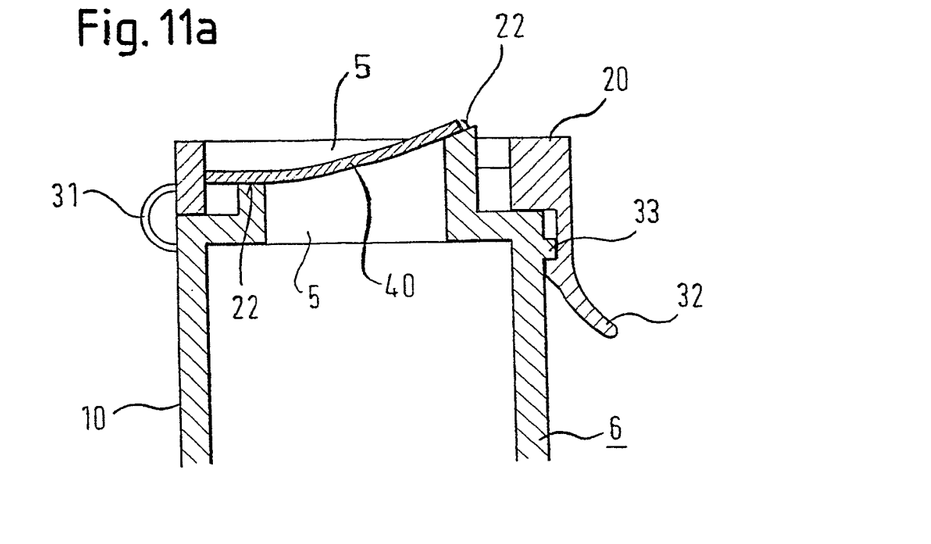
FIG. 11a shows a valve in accordance with a further embodiment of the present invention, in which the valve member is secured to the movable part of the inhalation therapy device in a closed state.
Figure 11B:
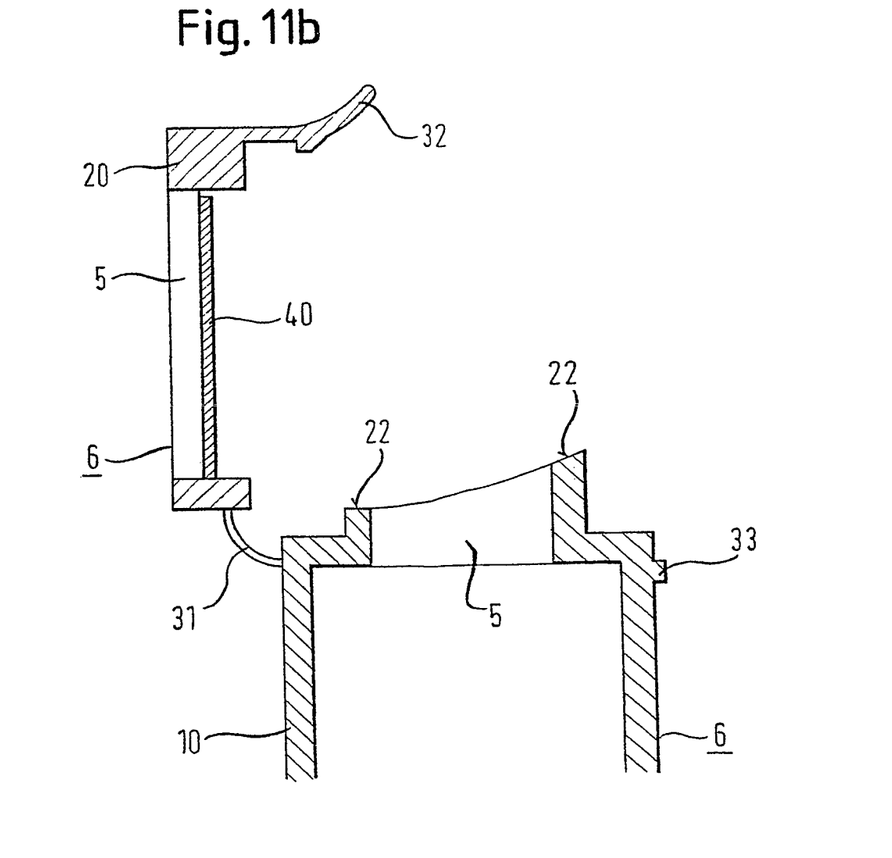
FIG. 11b shows a valve in accordance with the further embodiment of the present invention, in which the valve member is secured to the movable part of the inhalation therapy device in an opened state.

In a further advantageous embodiment, as shown in FIGS. 11a and 11b, the valve member is secured to the movable part 20 of the inhalation therapy device without a valve member positioning means. The valve member is attached to the stationary part 20 of the inhalation therapy device in such a way that, in the example shown here, the valve member abuts the valve seat 22 in a pre-tensioned manner and closes the opening 5 of the inhalation therapy device. The embodiment depicted here can be used as an exhalation valve in an inhalation therapy device. By appropriately designing the valve seat 22, the valve member 40 can abut the valve seat 22 even without pre-tension, for example if the valve seat 22 has a straight design. In an opened state, as shown in FIG. 11b, the valve member is spaced apart from the valve seat 22 such that both the valve member 40 and the valve seat 22 of the inhalation therapy device can be cleaned easily. The embodiment shown here can be modified in such a way that the movable part 20 of the inhalation therapy device can also be locked by means of two or more snap connections instead of by a film hinge. This makes it possible to replace the movable part and to hence replace a possible damaged valve member 40 without rendering the inhalation therapy device useless as such on account of a faulty valve member 40.

The invention claimed is:

1. An inhalation therapy device comprising:
   a nebulizer chamber,
   an aerosol generator arranged such as to emit a generated aerosol into said nebulizer chamber,
   at least one opening in a wall of said nebulizer chamber, and
   at least one valve arranged on said at least one opening in said wall of said nebulizer chamber,
   wherein said valve comprises:
   a valve seat,
   a resilient valve member and
   a valve member positioning means,
   said valve member positioning means being movable, relative to said valve seat, out of a first position and into a second position
      such that in the first position, said resilient valve member, in a flow-free state, is positioned on said valve seat by said valve member positioning means, so that said valve seat is provided on one side of said resilient valve member and said valve member positioning means is provided on an opposite side of said resilient valve member, and
      so that, in the second position which is different from said first position and in which said valve is in an opened state for cleaning said valve and in which said resilient valve member remains securely fixed on said valve, said resilient valve member is spaced apart from said valve seat, wherein in said second position said resilient valve member remains securely connected at a fixing point while the valve seat, the resilient valve member, and the valve member positioning means are accessible for cleaning without concealed areas, and
   wherein the valve member positioning means and the valve seat are attached to each other by a hinge and are configured to be moved apart relative to each other from said first position to said second position.

2. The inhalation therapy device according to claim 1, wherein the spacing apart is achieved by a fixing of the valve member.

3. The inhalation therapy device according to claim 1, wherein said valve member is attached in the vicinity of or to said valve member positioning means.

4. The inhalation therapy device according to claim 1, wherein said valve member is attached in the vicinity of or to said valve seat.

5. The inhalation therapy device according to claim 1, wherein said valve member is positioned with pre-tension on said valve seat.

6. The inhalation therapy device according to claim 5, wherein the pre-tension is produced by bending said valve member.

7. The inhalation therapy device according to claim 6, wherein said valve seat has a curved, rounded or sloping design so as to bend said valve member positioned on said valve seat to produce the pre-tension.

8. The inhalation therapy device according to claim 1, wherein a portion of said wall, in which said opening is disposed, is movable relative to said nebulizer chamber.

9. The inhalation therapy device according to claim 8, wherein the movable portion of said wall is designed as a lid of said nebulizer chamber.

10. The inhalation therapy device according to claim 9, wherein said lid is attached in a fold-down manner to a stationary part of said nebulizer chamber.

11. The inhalation therapy device according to claim 8, wherein said movable portion, in particular said lid, is attached in a fold-down manner by said hinge.

12. The inhalation therapy device according to claim 11, wherein said hinge is bi-stable.

13. The inhalation therapy device according to claim 8, wherein said valve seat is provided on said movable portion, in particular a lid, and said valve member positioning means is provided on a stationary part of said nebulizer chamber.

14. The inhalation therapy device according to claim 8, wherein said valve member positioning means is provided on said movable portion, in particular said lid, and said valve seat is provided on said stationary part of said nebulizer chamber.

15. The inhalation therapy device according to claim 1, wherein said movable portion, in particular on said lid, can be locked in a closed state by means of at least one snap connection.

16. The inhalation therapy device according to claim 1, wherein at least two of the valve seat, the valve member and the valve member positioning means are injection-moulded as a single part from different materials.

17. The inhalation therapy device according to claim 1, wherein the valve seat, the valve member and/or the valve member positioning means are produced in a two-component injection-moulding process.

18. The inhalation therapy device according to claim 1, wherein said valve member is essentially made of a softer material than said valve seat and/or said valve member positioning means.

19. The inhalation therapy device according to claim 1, wherein said valve member is essentially made of silicone rubber or thermoplastic elastomer.

20. The inhalation therapy device according to claim 1, wherein said valve seat comprises a circumferential sealing lip.

21. The inhalation therapy device according to claim 1, wherein said valve is an inhalation valve or an exhalation valve.

22. An inhalation therapy device comprising:
a nebulizer chamber,
an aerosol generator arranged such as to emit a generated aerosol into said nebulizer chamber,
at least one opening in a wall of said nebulizer chamber, and
at least one valve arranged on said at least one opening in said wall of said nebulizer chamber,
wherein said valve comprises:

a valve seat and a resilient valve member, said valve seat being movable, relative to said resilient valve member, out of a first position and into a second position such that in the first position, said resilient valve member, in a flow-free state, is positioned on said valve seat in a pre-tensioned manner by said valve seat and so that, in the second position which is different from said first position and in which said valve is in an opened state for cleaning said valve and in which said resilient valve member remains securely fixed on said valve, said resilient valve member is spaced apart from said valve seat, wherein a portion of said wall is movable relative to said nebulizer chamber, wherein in said second position said resilient valve member remains securely connected at a fixing point while the valve seat and the resilient valve member are accessible for cleaning without concealed areas, and wherein a stationary part of the wall and the valve seat are attached to each other by a hinge and are configured to be moved apart relative to each other from said first position to said second position while said resilient valve member remains securely connected at said stationary part.

23. The inhalation therapy device according to claim 22, wherein said opening is disposed, in said movable portion of said wall.

24. The inhalation therapy device according to claim 22, wherein the movable portion of said wall is designed as a lid of said nebulizer chamber.

25. The inhalation therapy device according to claim 24, wherein said lid is attached in a fold-down manner to a stationary part of said nebulizer chamber.

26. The inhalation therapy device according to claim 23 wherein said movable portion, in particular said lid, is attached in a fold-down manner by said hinge.

27. The inhalation therapy device according to claim 26, wherein said hinge is bi-stable.

28. The inhalation therapy device according to claim 22, wherein said valve seat is provided on said movable portion, in particular said lid, and said valve member is provided on said stationary part of said nebulizer chamber.

29. The inhalation therapy device according to claim 22, wherein the pre-tension is produced by bending said valve member.

30. The inhalation therapy device according to claim 22, wherein said valve seat has a curved, rounded or sloping design so as to bend said valve member positioned on said valve seat to produce the pre-tension.

31. The inhalation therapy device according to claim 22, wherein said movable portion, in particular on said lid, can be locked in a closed state by means of at least one snap connection.

32. The inhalation therapy device according to claim 22, wherein at least two of the valve seat, the valve member and the movable portion or a stationary part are injection-moulded as a single part from different materials.

33. The inhalation therapy device according to claim 22, wherein the valve seat, the valve member and/or the movable portion or a stationary part are produced in a two-component injection-moulding process.

34. The inhalation therapy device according to claim 22, wherein said valve member is essentially made of a softer material than said valve seat.

35. The inhalation therapy device according to claim 22, wherein said valve member is essentially made of silicone rubber or thermoplastic elastomer.

36. The inhalation therapy device according to claim 22, wherein said valve seat includes a circumferential sealing lip.

37. The inhalation therapy device according to claim 22, wherein said valve is an inhalation valve or an exhalation valve.

* * * * *